(12) United States Patent
Essayem et al.

(10) Patent No.: US 9,255,218 B2
(45) Date of Patent: Feb. 9, 2016

(54) METHOD FOR OBTAINING COMPOSITIONS OF BIOSOLVENTS BY ESTERIFICATION AND OBTAINED COMPOSITIONS OF BIOSOLVENTS

(75) Inventors: Nadine Essayem, Saint Just Chaleyssin (FR); Gilbert Sapaly, Lyons (FR); Thi Thu Ha Vu, Hanoi (VN); Thi Thu Trang Nguyen, Hanoi (VN); Thi Thuy Ha Nguyen, Hanoi (VN)

(73) Assignees: INSTITUT VIETNAMIEN DE CHIMIE INDUSTRIELLE, Hanö (VN); CENTRE NATIONAL DE LA RECHERCHE SCIENTIFIQUE (C.N.R.S), Paris (FR); UNIVERSITÉ CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 13/582,153

(22) PCT Filed: Mar. 3, 2011

(86) PCT No.: PCT/FR2011/050441
§ 371 (c)(1),
(2), (4) Date: Jan. 10, 2013

(87) PCT Pub. No.: WO2011/107712
PCT Pub. Date: Sep. 9, 2011

(65) Prior Publication Data
US 2013/0105738 A1 May 2, 2013

(30) Foreign Application Priority Data
Mar. 4, 2010 (FR) ........................ 10 51570

(51) Int. Cl.
*C09K 3/00* (2006.01)
*C07C 67/03* (2006.01)
*C07C 67/08* (2006.01)
*C09D 7/00* (2006.01)
*C09D 9/00* (2006.01)

(52) U.S. Cl.
CPC . *C09K 3/00* (2013.01); *C07C 67/03* (2013.01); *C07C 67/08* (2013.01); *C09D 7/001* (2013.01); *C09D 9/005* (2013.01)

(58) Field of Classification Search
CPC ........ C07C 67/03; C07C 67/08; C09D 7/001; C09D 9/005; C09K 3/00
USPC .................. 252/364; 516/29; 554/1; 560/129
See application file for complete search history.

(56) References Cited

U.S. PATENT DOCUMENTS

| 1,651,666 | A | 12/1927 | Buc |
| 4,608,202 | A | 8/1986 | Lepper et al. |
| 5,440,061 | A | 8/1995 | Gibson |
| 6,191,087 | B1 * | 2/2001 | Opre et al. ..................... 510/201 |
| 6,284,720 | B1 | 9/2001 | Opre |
| 6,706,259 | B1 | 3/2004 | Gardner et al. |
| 2005/0143599 | A1 | 6/2005 | Wicki et al. |

FOREIGN PATENT DOCUMENTS

GB   1 282 926 A   7/1972

OTHER PUBLICATIONS

Wildes, S.; Chemical Health and Safety, 2002, p. 24-26.*
Garcia, J.I., et al.; Green Chemistry, 2010, vol. 12, p. 426-434.*
Okayasu, T., et al.; Chemical Communications, 2009, p. 4708-4710.*
Citgo, Benzene Material Safety Data Sheet, 2009, p. 1-10.*
EMD, Chloroform Material Safety Data Sheet, 2009, p. 1-8.*
IUPAC Compendium of Chemical Terminology, 2nd ed. (the "Gold Book"), 1997, Fatty Acids entry, p. 1-2.*
Spear, S. et al.; Green Chemistry, 2007, vol. 9, p. 1008-1015.*
Rathin, et al., "Lactic acid: recent advances in products, processes and technologies—a review", Journal of Chemical Technology and Biotechnology, vol. 81, May 2, 2006, pp. 1119-1129, XP002603807.
International Search Report issued on Jun. 10, 2011 for International Application No. PCT/FR2011/050441.

* cited by examiner

*Primary Examiner* — Robert Jones, Jr.
(74) *Attorney, Agent, or Firm* — Knobbe Martens Olson & Bear, LLP

(57) ABSTRACT

A method for synthesizing a composition comprising at least one acid ester stemming from the biomass and an organic biosolvent is provided. The method comprises the esterification reaction between at least one acid stemming from the biomass and at least one alcohol, in the presence of an acid catalyst and of the organic biosolvent, the organic biosolvent being selective of the ester or of the esters formed relatively to the acid or to the starting acids and non-miscible with the alcoholic solution of the acid stemming from the biomass.

13 Claims, 1 Drawing Sheet

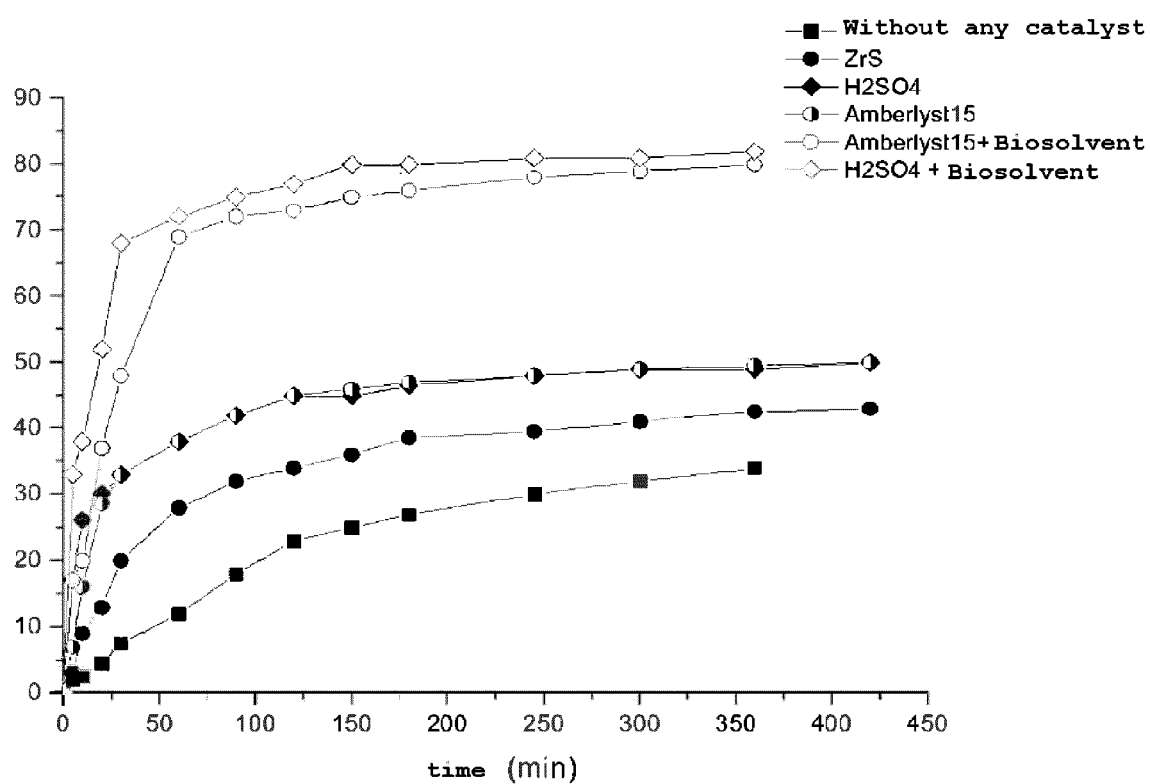

METHOD FOR OBTAINING COMPOSITIONS OF BIOSOLVENTS BY ESTERIFICATION AND OBTAINED COMPOSITIONS OF BIOSOLVENTS

CROSS REFERENCE TO RELATED APPLICATIONS

This application is the U.S. National Phase of International Application No. PCT/FR2011/050441, filed Mar. 3, 2011, designating the U.S. and published as WO 2011/107712 on Sep. 9, 2011 which claims the benefit of French Patent Application No. 10 51570 filed Mar. 4, 2010.

FIELD OF THE INVENTION

The invention relates to a novel method for preparing compositions of biosolvents, by esterification in a step from acids stemming from the biomass. The invention also relates to the thereby obtained compositions of biosolvents. The invention also relates to a method for adding value to carboxylic acids stemming from the biomass, preferably fermental acids.

BACKGROUND OF THE INVENTION

Solvents form a class of substances widely used in many economical sectors where they play diverse roles. These are liquids capable of dissolving, diluting or extracting other compounds without generating chemical modifications. However, traditional solvents are general volatile organic compounds, harmful for health and for the environment. Environmental regulations nowadays call for the use of substitution solvents, notably in industrial applications. In this context, novel solvents called biosolvents, stemming from renewable, non-toxic and biodegradable raw materials, have appeared on the market. They have the advantage of providing an alternative to fossil, notably petroleum resources on the one hand and a positive environmental balance on the other hand.

The main biosolvents involved in cleaning formulations, formulations for plant health products, printing inks, paints, varnishes or bituminous binders are esters of fermental organic acids such as ethyl lactate, fatty acid esters, ethanol, terpene derivatives, glycerol or sugars derivatives. Among these biosourced compounds, ethyl lactate and fatty acid esters are known for their solvent properties, used alone or as mixtures. From U.S. Pat. No. 6,284,720, a composition of biosolvents is notably known, comprising from 40 to 70% by weight of a $C_1$-$C_4$ lactic acid ester, preferably ethyl lactate, and from 1 to 30% by weight of a $C_{16}$-$C_{20}$ ester of a $C_1$-$C_4$ fatty acid having a melting point below $-10°$ C., preferably ethyl esters (which have the advantage of being 100% biosourced, ethanol being produced by fermentation of sugars while methanol stems from petroleum) or methyl esters of fatty acids from a vegetable oil. The composition may further comprise additives, surfactants . . . . From U.S. Pat. No. 6,191,087, a biosolvent composition is also known comprising from 10 to 60% by weight of a $C_{16}$-$C_{20}$ fatty acid ester having a melting point below $-10°$ C., from 20 to 75% by weight of a $C_1$-$C_4$ lactic acid ester, from 0 to 20% by weight of a surfactant, from 0 to 20% by weight of a thickener and from 0 to 50% by weight of an organic solvent. The publication of Datta et al. (Journal of Chemical Technology and Biotechnology, 2006, 81, 1119-1129) describes the different applications of lactic acid and of its derivatives, notably the use of ethyl lactate in compositions of biosolvents.

The compositions of biosolvents are obtained by mixing ethyl lactate with the desired fatty acid esters. Ethyl lactate is produced by esterification of lactic acid with ethanol. However, a major problem of this reaction is that it is balanced. It is therefore necessary to displace the equilibrium for obtaining a suitable yield. This is notably possible by using excess ethanol or by continuously drawing off the water formed during the reaction. The solutions presently set into place for solving this major problem are at the origin of a substantial increase in the cost of ethyl lactate. Another problem is the oligomerization of lactic acid during the reaction.

Many investigations have been conducted for finding a remedy to these problems and to improve the yield in ethyl lactate. From GB 1,282,926, a method for separating acids is notably known, comprising esterification of the acids, separation of the obtained esters and recovery of the corresponding acid. The described method comprises the following steps: an aqueous solution containing lactic acid is mixed with a water-miscible alcohol. The resulting solution is extracted by moderately heating it with an organic solvent non-miscible with water. The lactic acid contained in the aqueous phase is transformed into a lactic acid ester, which ester passes into the organic phase. This organic phase is then distilled in order to retrieve the non-miscible solvent. The residue is then distilled in order to recover the lactic acid ester in a pure form and is then transformed into an acid. With this method it is therefore possible to extract the formed ester from the aqueous phase which displaces the equilibrium towards the formation of the ester. However, the solvents used are non-biological organic solvents and some of them are toxic (benzene, chloroform . . . ).

From U.S. Pat. No. 1,651,666, a method for ester preparation by reaction between a mixture of an alcohol, an acid and a solvent of the corresponding ester is known. However, the solvent of the ester is an oil derived from petroleum with a high boiling point. With this method, it is not possible to obtain a biosolvent composition comprising esters in a single step.

From US 2005/0143599, the use of a solvent derived from petroleum is also known for esterifying and extracting an acid diluted in water. This method is specifically aimed at the separation of acids and does not allow preparation of a biosolvent comprising esters in a single step.

From U.S. Pat. No. 5,723,639, a method for preparing ethyl lactate is known by reacting ammonium lactate with ethanol, applying a pervaporation membrane. This pervaporation membrane gives the possibility of letting through the water and ammonia formed but does not let through the alcohol and ester formed. Thus, one has a continuous extraction of water. The publication of Budd et al. (Ind. Eng. Chem. Res., 2004, 43, 1863-1867) also describes the use of a pervaporation membrane for the esterification reaction between lactic acid and ethanol. However, such membranes are relatively fragile and of a high cost. The method for preparing ethyl lactate by means of this method is therefore not very economical.

From WO 2004/052826, a method for preparing ethyl lactate by esterification between lactic acid and ethanol is known. This method is based on the existence of a water/ethanol azeotrope. During the process, a water-ethanol gas mixture is extracted continuously, this extract is dehydrated and allows recovery of an ethanol flow which may be recycled. Once again, this method requires additional equipment and treatments for displacing the equilibrium, which increases the production costs of ethyl lactate.

Finally, from WO 01/47860, a method for producing ethyl lactate in two steps is known. The first step consists in a transformation, with removal of water, of a composition of lactic acid into an oligomeric composition of lactic acid. This first step allows removal of the water which may be formed. The second step consists in an esterification of all or part of the contained lactic acid, in monomeric, dimeric, oligomeric or polymeric form, by means of a transesterification catalyst. This method has the drawback of being carried out in two steps which increases the reaction times as well as the costs of the method.

Thus, since the filing of patent GB 1,282,926, methods for synthesis of ethyl lactate by esterification have become complicated, leading to two-step methods or to methods using additional equipment or even costly and sensitive equipment (pervaporation membrane).

The compositions of biosolvents comprising ethyl lactate are obtained in 2 steps, a first step for forming ethyl lactate and a second step for mixing this lactate with biosolvents. Such two-step methods substantially increase the cost price of the final composition, further requiring complementary steps, notably for purifying ethyl lactate.

SUMMARY OF INVENTION

Therefore there is a need for finding a method for preparing a biosolvent based on ethyl lactate which is more competitive both in terms of environmental waste and in terms of costs and notably for providing a method for synthesizing compositions of biosolvents in a single step.

An object is also finding such a method which may be applied for other acids stemming from the biomass.

An object of the present invention is to provide a method for synthesizing biosolvent compositions in one step from organic acids stemming from the biomass which gives the possibility of addressing the aforementioned drawbacks and notably, neither requiring the use of excess alcohol, nor continuous extraction of the water formed.

Another object of the present invention is to provide a method for adding value to biomass, and notably to acids stemming from the biomass, for example produced as a result of a fermentation process, in a composition of biosolvents.

Other objects will further become apparent in the light of the description.

DETAILED DESCRIPTION OF THE EMBODIMENTS

The present invention relates to a method for synthesizing a composition comprising at least one ester of an acid stemming from the biomass and at least one organic biosolvent, said method comprising an esterification reaction between at least one acid stemming from the biomass and at least one alcohol, in the presence of an acid catalyst and of the organic biosolvent, said organic biosolvent being selective of the ester formed with respect to the starting acid and notably nonmiscible with the alcoholic solution of acids stemming from the biomass.

Thus, the method according to the invention comprises the mixture of at least one acid stemming from the biomass, at least one alcohol and one organic biosolvent, the acid and the alcohol react in order to form an ester which will be solubilized in the organic biosolvent. By separating both phases, the acid/alcohol mixture on the one hand, the organic biosolvent/ester mixture on the other hand, it is possible to obtain the organic biosolvent/ester mixture corresponding to the composition according to the invention.

By biomass is meant the whole of the organic material (carbohydrate) of vegetable or animal origin, but also any product or liquid effluent stemming from its mechanical, thermochemical, enzymatic transformation or from fermental methods as well as from their mixtures.

The acids may stem from the biomass through fermentation processes (notably of sugars), for example lactic, citric, succinic, levulinic acids or by pressing the biomass, for example aconitic acid stemming from the pressing of sugar cane.

Before applying the method of the invention, the acids may be separated from the biomass by methods known to one skilled in the art.

The acids may be applied either purified or non-purified. Thus the acids, notably non-purified, may comprise water, notably in amounts related to their formation process.

The alcohols may also be applied either purified or non-purified. Thus the alcohols may comprise water, notably in amounts related to their formation process.

For the method of the invention, by <<organic biosolvents selective of the ester or of the esters formed with respect to the starting acid or acids>> is meant an organic biosolvent which solubilizes the ester or esters and which is insoluble in the alcohol/acid mixture. The biosolvent is therefore not soluble in the alcohol/acid mixture thereby forming a biphasic medium. The formed ester or esters are much more soluble in the organic biosolvent than in the alcohol/acid mixture thereby allowing extraction of this(these) ester(s) in the biosolvent. The ester formed notably has greater solubility in the organic biosolvent than in the starting alcohol/acid mixture.

The biphasic medium advantageously allows solubilization and extraction of this(these) esters by phase transfer.

The greater solubility of the ester or of the esters formed in the biosolvent than in the alcohol/acid mixture allows displacement of the equilibrium and collection of an organic phase sufficiently rich in ester so that it is not necessary to recycle or reprocess the aqueous phase. One skilled in the art, because of his general knowledge, will be able to determine whether the biosolvent has insolubility towards the acid plus alcohol mixture which is sufficient for being used in the method of the invention. Thus, all the biosolvents which are not soluble in the alcoholic acid solution stemming from the biomass, forming a biphasic reaction medium and capable of solubilizing the ester or the esters formed by reaction between the acid and the alcohol, may be used for the method of the invention.

A biphasic mixture will be formed between the {alcohol+acid stemming from the biomass} on the one hand and the organic biosolvent on the other hand. Without being bound by any theory, it appears that the alcohol and the acid react in order to give an ester which will be solubilized, as soon as it is formed in the organic biosolvent. This solubilization of the ester formed causes displacement of the reaction in favor of the formation of the ester, thereby allowing an increase in the ester yield.

The biphasic nature of this reaction mixture is also advantageous since it allows separation of the phases if necessary, for example by methods well known to one skilled in the art, for example by decantation and/or by adding water to the medium which allows removal of residual acids and alcohols, and a composition of biosolvents may be obtained comprising as a mixture, the ester(s) formed and the organic biosolvent. This composition may be directly used without requiring any additional step, notably a purification step.

The alcohol/acid mixture may also comprise water.

According to an embodiment, the organic biosolvent is not pelargonic acid.

According to the method of the invention, the organic biosolvents which may be used, are selected from fatty acid esters of natural origin and glycerol alkyl ethers, either alone or as a mixture.

By fatty esters are meant aliphatic esters having a carbon chain with 4 to 28 carbon atoms. Preferentially, the fatty acids are selected from aliphatic esters having a carbon chain with 12 to 22 carbon atoms.

They may be obtained by known methods such as for example transesterification of fats of vegetable or animal origin by methanol or ethanol (usual methods for synthesizing biodiesel fuel).

According to the method of the invention, the fatty acid esters of natural origin are preferably esters produced by transesterification with ethanol or methanol of vegetable oil or animal fats, preferably fatty acid ethyl and methyl esters, either alone or as a mixture, notably $C_{12}$-$C_{22}$ fatty acid methyl or ethyl esters.

According to the method of the invention, the fatty acid esters are preferably selected from methyl or ethyl esters of rape seed oil, palm oil, jatrofa oil, olive oil, sesame oil, ground nut oil, maize oil, poppy oil, safflower oil, soya bean oil, sunflower oil, used vegetable oils or animal fats, either alone or as a mixture.

According to the invention the glycerol ethers are ethers of glycerol with a fatty chain. Preferably, the glycerol ethers are selected from mono-, di- or tri-alkyl glycerol ethers, with alkyl chains, preferably saturated or unsaturated $C_{12}$-$C_{22}$ alkyl chains, either alone or as a mixture.

By unsaturated alkyl chain is meant an alkyl chain which is totally or partly unsaturated.

The amount of organic biosolvent used in the present method has to be sufficient in order to allow solubilization/extraction of the ester(s) formed.

The properties of the biosolvent composition, either obtained or which may be obtained, with the present method, depend on the proportion of its different constituents. Thus, the amount of organic biosolvent is determined according to the desired properties for the composition.

Preferably, the organic biosolvent/{alcohol+acid stemming from the biomass} mixture mass ratio is greater than or equal to 1:1.

Preferably, the acid from the biomass is notably an acid from the fermentation of biomass.

According to the method of the invention, the carboxylic acid (mono-acid, diacid or triacid) stemming from the biomass (preferably obtained via a fermental route) is selected from lactic acid, levulinic acid, behenic acid, gadoleic acid, succinic acid, adipic acid, glutaric acid, citric acid, aconitic acid, itaconic acid, alone or as a mixture.

The method of the present invention may equally be carried out by homogeneous or heterogeneous acid catalysis.

In an embodiment, the catalyst is a homogeneous acid catalyst. In a particular embodiment, the homogeneous acid catalyst is selected from strong mineral acids, preferably sulphuric acid, methane-sulfonic acid, triflic acid, trifluoromethane-sulfonic acid, hydrochloric acid, alone or as a mixture.

By strong acids are meant homogeneous or heterogeneous acids characterized by a Hammett acidity value —Ho>3.

In an embodiment, the catalyst is a heterogenous acid catalyst.

In an embodiment, the heterogeneous acid catalyst is selected from the group formed by acid ion exchange resins, preferably sulfonic ion exchange resins, notably those for which the base is a macro-crosslinked copolymer of styrene and divinylbenzene, with a variable functional group capacity (Amberlyst® 15, 35 . . . marketed by Rohm & Hass). It is also possible to use in the methods with perfluorated ion exchange resins of the Nafion® type marketed by du Pont de Nemours.

In another embodiment, the catalyst is selected from the group formed by heteropolyacids supported on coal, preferably heteropolyacids with a Keggin structure $H_3PW_{12}O_{40}$, $H_4SiW_{12}O_{40}$, $H_3PMo_{12}O_{40}$, $H_4SiMo_{12}O_{40}$; alkaline acid salts of these heteropolyacids preferably of formula $AxH_{3-x}PM_{12}O_{40}$ avec $A=Cs^+, K^+, Rb^+, NH_4^+$ et $M=W$ or Mo; or of formula $AxH_4-xSiM_{12}O_{40}$ $A=Cs^+, K^+, Rb^+, NH_4^+$ et $M=W$ or Mo; catalysts based on sulfonated coal; catalysts based on an oxide support (zirconium, titanium, aluminum, niobium oxide) modified by oxoanions (sulfate, tungstate, phosphate . . . ); catalysts of the acid zeolite type (H-Beta, H-ZSM5 . . . ), silicas-aluminas or other acid mixed oxides, cationic clays.

Preferably, the catalyst is selected from the group formed by heteropolyacids supported on coal, preferably hétéropolyacides with a Keggin structure $H_3PW_{12}O_{40}$, $H_4SiW_{12}O_{40}$, $H_3PMo_{12}O_{40}$, $H_4SiMo_{12}O_{40}$; alkaline acid salts of these heteropolyacids preferably of formula $AxH_3-xPM_{12}O_{40}$ with $A=Cs^+, K^+, Rb^+, NH_4^+$ and $M=W$ or Mo; or of formula $AxH_4-xSiM_{12}O_{40}$ $A=Cs^+, K^+, Rb^+, NH_4^+$ and $M=W$ or Mo; catalysts based on sulfonated coal; catalysts based on an oxide support (zirconium, titanium, aluminum, niobium oxide) modified by oxoanions (sulfate, tungstate, phosphate . . . ); catalysts of the acid zeolite type (H-Beta, H-ZSM5 . . . ).

One of the major advantages of the use of heterogeneous acid catalysts is their easy and rapid removal from the reaction medium. Indeed, a simple filtration will be sufficient for removing the catalysts from the obtained product.

The catalyst, either homogeneous or heterogeneous, is present in a sufficient amount, notably comprised between 0.1 and 10% by weight based on the acid or on the mixture of acids stemming from the biomass, preferably between 0.1 to 5% by weight, more preferentially about 1% by weight.

Preferably, the alcohol is selected from ethanol, methanol, propanol, butanol, alone or as a mixture.

A priori there is no upper limit as regards the amount of alcohol used in the method. Indeed, the larger the amount of alcohol, the larger is the reactivity and therefore the ester yield. However, the final biosolvent composition may comprise traces of alcohol which, if they are too significant, may modify its properties. Thus, the desired properties for the final biosolvent composition may be at the origin of a limitation of the amount of alcohol used.

In an embodiment, the alcohol/acid ratio is advantageously comprised between 1 and 5, preferably comprised between 2 and 5, for example it is about 3.

The method of the present invention may be conducted at various temperatures. The reaction rate depends on the temperature at which it is applied, thus the lower the temperature the slower is the reaction. On the contrary, an increase in the temperature allows an increase in the reaction rate.

The temperature for applying the method of the present invention inter alia depends on the nature of the compounds set into play and notably on their thermal stability. One skilled in the art is capable of determining the optimum temperature at which the method has to be carried out.

Preferably, the method is applied at the boiling temperature of the reaction mixture, the application at such a temperature representing a good compromise between reaction rate and reaction conditions. However, as mentioned above, the method may be applied at a lower temperature hence a reduction in the reaction rate. The method may also be applied at a temperature above the boiling temperature of the mixture while remaining at a temperature below the limiting stability temperature of the catalyst.

For example, when the catalyst is a homogeneous catalyst, the temperature may be comprised between 40° C. and 200° C.

For example, when the catalyst is a heterogeneous catalyst, the temperature may be comprised between 40° C. and the maximum stability temperature of the catalyst.

For Amberlyst®, the maximum stability temperature is of the order of 130° C.

For example for heteropolyacids supported on coal, the temperature is preferably comprised between 40° C. and 300° C.

In the same way, the method may be carried out in a diverse pressure range.

In an embodiment, the method is carried out under atmospheric pressure, under reduced pressure or under the autogenous pressure of the medium. Preferably, the method is carried out under atmospheric pressure.

In an embodiment of the invention, the method further comprises a step for recovering the biosolvent composition formed. In an embodiment, this recovery step is a decantation.

In an embodiment of the invention, the method further comprises a step for removing the catalyst. This step for removing the catalyst may be carried out by any methods known to one skilled in the art. For the case of heterogeneous acid catalysts, the removal of the catalyst may be achieved by simple filtration.

The present invention also relates to the biosolvent composition obtained by the method of the present invention.

Advantageously, the composition obtained or which may be obtained by the method of the invention, may notably be used as products for cleaning printing inks, for degreasing metal parts, solvents for nail varnish, cleaning products for coatings, solvents for paint, like solvents in printing ink formulations, formulations of pesticides and plant protection adjuvants, domestic or industrial cleaning products, in cosmetic products, bituminous binders, formulations of <<siccative>> esters.

The present invention also relates to a method for adding value to carboxylic acids stemming from the biomass by esterification applying the method of the present invention for obtaining biosolvent compositions.

With the following examples, it is possible to illustrate the method of the invention and its advantages. The latter are given as an illustration without however being limiting.

FIG. 1 illustrates the ethyl lactate yield, versus time, for the esterification reaction between lactic acid and ethanol, without any catalyst or biosolvent (a), in the presence as a catalyst of sulfated zirconia and without any biosolvent (b), in the presence of sulfuric acid as a catalyst and without any biosolvent (c), in the presence of Amberlyst-15® as a catalyst and without any biosolvent (d), in the presence of Amberlyst-15® as a catalyst and of biosolvent (e), in the presence of sulfuric acid as a catalyst and of biosolvent (f).

COMPARATIVE EXAMPLES

The examples were carried out with lactic acid in the presence of ethanol. The experiments were conducted with different catalysts or in the absence of any catalyst or in the absence of any organic biosolvent.

Example a

Method Carried Out in the Absence of any Catalyst and of any Organic Biosolvent

The synthesis of ethyl lactate is achieved in a Pyrex® flask equipped with a condenser.

The following amounts of reagents are introduced into the reactor: 66.7 g of ethanol, 39.1 g of lactic acid (LA) (EtOH/LA molar ratio=3.3). The reaction medium is stirred by means of a magnetic stirrer. The reaction medium is brought to the reaction temperature by means of a regulated 80° C. oil bath. Progress of the reaction is followed by taking samples. The molar yield of ethyl lactate is determined by gas chromatography (GC) analysis.

The ethyl lactate yield versus the duration of the reaction is illustrated in FIG. 1, curve a.

Example b

Method Carried Out in the Presence of Sulfated Zirconia as a Catalyst and in the Absence of any Organic Biosolvent The synthesis of ethyl lactate is carried out in a Pyrex® flask equipped with a condenser.

The following amounts of reagents are introduced into the reactor: 66.7 g of ethanol, 39.1 g of lactic acid (EtOH/LA molar ratio=3.3). 1.2 g of sulfated zirconia (0.75 mmol of $H^+$), dehydrated beforehand for one night in an oven at 110° C., is added to the reagents. The reaction medium is stirred by means of a magnetic stirrer. The reaction medium is brought to the reaction temperature by means of a regulated 80° C. oil bath. Progress of the reaction is followed by taking samples. The molar ethyl lactate yield is determined by GC analysis.

The ethyl lactate yield versus the duration of the reaction is illustrated in FIG. 1, curve b.

Example c

Method Carried Out in the Presence of Sulfuric Acid as a Catalyst and in the Absence of any Organic Biosolvent The synthesis of ethyl lactate is carried out in a Pyrex® flask equipped with a condenser.

The following amounts of reagents are introduced into the reactor: 66.7 g of ethanol, 39.1 g of lactic acid (EtOH/LA molar ratio=3.3). 0.33 g of 96% sulfuric acid (6.46 mmol of $H^+$), is added to the reagents. The reaction medium is stirred by means of a magnetic stirrer. The reaction medium is brought to the reaction temperature by means of a regulated 80° C. oil bath. Progress of the reaction is followed by taking samples. The molar ethyl lactate yield is determined by GC analysis.

The ethyl lactate yield versus the duration of the reaction is illustrated in FIG. 1 curve c.

Example d

Method Carried Out in the Presence of Amberlyst-15® as a Catalyst and in the Absence of any Organic Biosolvent The synthesis of ethyl lactate is carried out in a Pyrex® flask equipped with a condenser.

The following amounts of reagents are introduced into the reactor: 66.7 g of ethanol, 39.1 g of lactic acid (EtOH/LA molar ratio=3.3). 1.4 g of Amberlyst-15® (6.6 mmol of H⁺), dehydrated beforehand for one night in an oven at 110° C., is added to the reagents. The reaction medium is stirred by means of a magnetic stirrer. The reaction medium is brought to the reaction temperature by means of a regulated 80° C. oil bath. Progress of the reaction is followed by taking samples. The molar ethyl lactate yield is determined by GC analysis.

The ethyl lactate yield versus the duration of the reaction is illustrated in FIG. 1, curve d.

Exemplary Methods According to the Invention:

The examples which follow were carried out with lactic acid and ethanol in the presence of a biosolvent, according to the present invention.

Example d'

Preparation of the Biosolvent: Rape Seed Oil Methyl Ester

The following reagents are mixed in a Pyrex® flask: 330 g of rape seed oil, 120 g of MeOH, 3 g of KOH. Stirring is ensured by means of a mechanical stirrer. The flask, equipped with a condenser is placed in a regulated 80° C. oil bath. The reaction is stopped after 2 h 30 mins, the methyl ester is separated from glycerol by decantation. GC analysis of the methyl ester phase is performed in order to check whether the transformation is total.

Example e

Method Carried Out in the Presence of Amberlyst-15® as a Catalyst and of an Organic Biosolvent The synthesis of ethyl lactate is carried out in a Pyrex® flask equipped with a condenser.

The following amounts of reagents are introduced into the reactor: 66.7 g of ethanol, 39.1 g or lactic acid (EtOH/LA=3.3). 34 g of rape seed oil methyl esters obtained according to Example d' (biosolvent) are introduced into the flask. In a Pyrex® flask, 1.4 g of Amberlyst-15® (6.6 mmol of H⁺), dehydrated beforehand for one night in an oven at 110° C., is added to the reagents. The reaction medium is stirred by means of a magnetic stirrer. The reaction medium is brought to the reaction temperature by means of a regulated 80° C. oil bath. Progress of the reaction is followed by taking samples. The molar ethyl lactate yield is determined by GC analysis.

The ethyl lactate yield versus the duration of the reaction is illustrated in FIG. 1, curve e.

Example f

Method Carried Out in the Presence of Sulfuric Acid as a Catalyst and of an Organic Biosolvent The synthesis of ethyl lactate is carried out in a Pyrex® flask equipped with a condenser.

The following amounts of reagents are introduced into the reactor: 66.7 g of ethanol, 39.1 g of lactic acid (EtOH/LA molar ratio=3.3). 34 g of rape seed oil methyl esters obtained according to Example d' (biosolvent) are introduced. 0.33 g of 96% $H_2SO_4$ (6.46 mol of H⁺) are added to the reagents. The reaction medium is stirred by means of a magnetic stirrer. The reaction medium is brought to the reaction temperature by means of a regulated 80° C. oil bath. Progress of the reaction is followed by taking samples. The molar ethyl lactate yield is determined by GC analysis.

The ethyl lactate yield versus the duration of the reaction is illustrated in FIG. 1, curve f.

Study of the Results Obtained by the Various Methods

FIG. 1, grouping the results from the different examples, actually shows that the use of a catalyst allows an increase in the ethyl lactate yield when the biosolvent is used.

FIG. 1 also shows the influence of the use of the biosolvent and of the catalyst in the method. Thus an increase in the yield is noted after 350 minutes, by 30% (comparison of curves c and d and e and f).

It is interesting to note that the nature of the either homogeneous (of the sulfuric acid type) or heterogeneous (of the Amberlyst-15® type) catalyst has no influence on the obtained yield (comparison of curves e and f).

Finally, FIG. 1 shows that the ethyl lactate appearance rate is much larger in the presence of a catalyst and of a biosolvent.

What is claimed is:

1. A method for synthesizing a composition comprising at least one acid ester stemming from a biomass and an organic biosolvent selected from fatty acid esters of natural origin or mixtures thereof, comprising:
    an esterification of at least one acid stemming from the biomass with at least one alcohol, in the presence of an acid catalyst and of the organic biosolvent, said organic biosolvent being selective of the ester formed relative to the starting acid, and non-miscible with the alcoholic solution of acid stemming from the biomass,
    wherein the esterification happens in a single step, and
    wherein the method does not further comprise an additional purification step.

2. The method according to claim 1, wherein the ester formed has greater solubility in the organic biosolvent than in the alcohol/starting acid mixture.

3. The method according to claim 1, wherein the alcohol/acid mixture comprises water.

4. The method according to claim 1, wherein the organic biosolvent is selected from aliphatic esters having a carbon chain with 12 to 22 carbon atoms.

5. The method according to claim 1, wherein the organic biosolvent is selected from selected from the group consisting of fatty acid methyl or ethyl esters, and mixtures thereof.

6. The method according to claim 1, wherein the organic biosolvent is selected from the group consisting of methyl or ethyl esters stemming from rape seed oil, palm oil, jatrofa oil, olive oil, sesame oil, ground nut oil, maize oil, poppy seed oil, safflower oil, soya bean oil, sunflower oil, used vegetable oils or animal oils, and mixtures thereof.

7. The method according to claim 1, wherein the alcohol is selected from the group consisting of ethanol, methanol, propanol, butanol, and mixtures thereof.

8. The method according to claim 1, wherein the acid stemming from the biomass is selected from the group consisting of lactic acid, levulinic acid, behenic acid, gadoleic acid, succinic acid, aconitic acid, itaconic acid, glutaric acid, and mixtures thereof.

9. The method according to claim 1, wherein the catalyst is a homogeneous acid catalyst or a heterogeneous acid catalyst.

10. The method according to claim 9, wherein the catalyst is a sulfonic resin.

11. The method according to claim 1, wherein the weight ratio between the alcohol and the acid is comprised between 1 and 5.

12. The method according to claim 1, wherein the amount of catalyst is comprised between 0.1 and 10% by weight based on the acid or on the mixture of starting acids.

13. The method according to claim 1, wherein the organic biosolvent/{alcohol+acid stemming from the biomass} mixture mass ratio is greater than or equal to 1:1.

* * * * *